US00RE38324E

(19) United States
(12) Reissued Patent
Hollingworth

(10) Patent Number: US RE38,324 E
(45) Date of Reissued Patent: Nov. 18, 2003

(54) PROCESS FOR THE PREPARATION OF HYDROXY SUBSTITUTED GAMMA BUTYROLACTONES

(75) Inventor: Rawle I. Hollingworth, Haslett, MI (US)

(73) Assignee: Board of Trustees of Michigan State University, East Lansing, MI (US)

(21) Appl. No.: 10/109,487

(22) Filed: Mar. 28, 2002

Related U.S. Patent Documents

Reissue of:
(64) Patent No.: 5,808,107
Issued: Sep. 15, 1998
Appl. No.: 08/962,365
Filed: Oct. 31, 1997

(51) Int. Cl.[7] ..... C07D 307/32; C07D 307/33; C07C 69/675; C07C 27/06; C07C 27/08

(52) U.S. Cl. ..... 549/323; 549/326; 560/186; 560/858; 560/864

(58) Field of Search ..... 549/323, 326; 560/186; 568/858, 864

(56) References Cited

U.S. PATENT DOCUMENTS 2,683,721 A * 7/1954 Schlesinger et al. ..... 549/307
3,024,250 A * 3/1962 Klein et al. ..... 549/319
3,868,370 A * 2/1975 Smith ..... 549/326
3,997,569 A * 12/1976 Powell ..... 549/273
4,105,674 A * 8/1978 De Thomas et al. ..... 549/325
4,155,919 A * 5/1979 Ramioulle et al. ..... 549/508
4,772,729 A * 9/1988 Rao ..... 549/326
4,940,805 A * 7/1990 Fischer et al. ..... 549/326
4,994,597 A * 2/1991 Inoue et al. ..... 558/342
5,087,751 A * 2/1992 Inoue et al. ..... 564/192
5,292,939 A * 3/1994 Hollingsworth ..... 562/515
5,319,110 A * 6/1994 Hollingsworth ..... 249/313
5,374,773 A * 12/1994 Hollingsworth ..... 562/515
5,502,217 A * 3/1996 Fuchikami et al. ..... 549/325

OTHER PUBLICATIONS

Arth et al., Liebigs Ann., pp. 2037–2042, 1995.*
Tandon et al., J. Org. Chem., 48, pp. 2767–2769, 1983.*
Boger et al., J. Org. Chem., 46, pp. 1208–1210, 1981.*
Herradon, Tetrahedron: Asymmetry, 2(3), pp. 191–194, 1991.*
Hanessian et al., Can J. Chem., pp. 2146–2147, 1984.*

* cited by examiner

*Primary Examiner*—Ba K. Trinh
(74) *Attorney, Agent, or Firm*—Ian C. McLeod

(57) ABSTRACT

Preparation of 4-hydroxy substituted butyrolactones is described. A process for the preparation of 3-hydroxybutyrolactone, 1.2.4-trihydroxybutane and 3,4-dihydroxy acid methyl ester from malic acid is particularly described. The preparation of 4-hydroxymethyl-4-hydroxybutyric acid -1-methyl ester and 4-hydroxymethyl butyrolactone is particularly described. The compounds are intermediates to various pharmaceutical and agricultural products.

22 Claims, 4 Drawing Sheets

(S)-3-hydroxy gamma butyric acid lactone (Crude product from reduction of L-malic acid dimethyl ester)

* =impurity

There is a small amount of triol in the product

PROCESS FOR THE PREPARATION OF HYDROXY SUBSTITUTED GAMMA BUTYROLACTONES

Matter enclosed in heavy brackets [ ] appears in the original patent but forms no part of this reissue specification; matter printed in italics indicates the additions made by reissue.

BACKGROUND OF THE INVENTION (1) Summary of the Invention

The present invention relates to the preparation of hydroxy substituted gamma butyrolactones. In particular, the present invention relates to a process for the preparation of isomers, in the (R) or (S) form. Further, the present invention relates to the preparation of 3 hydroxybutyrolactone and derivatives thereof such as 1,2,4-trihydroxybutane and 3,4-dihydroxybutyric acid-1-methyl ester from malic acid. Further still, the present invention relates particularly to the preparation of 4-hydroxy methyl butyrolactone from 4-hydroxybutane dicarboxylic acid dimethyl ester. The compounds as the isomers are particularly useful as intermediates for pharmaceuticals, agrochemicals favors and fragrances.

(2) Description of Related Art

U.S. Pat. Nos. 4,994.597 and 5,087,751 to Inone et al describe derivatives of 3,4-dihydroxybutyric acid. The pro ass for preparing the acid is different from the present invention involving a reaction of metal cyanide and a 3,4-dihydroxy butyl chloride and then hydrolyzing. The acid is an intermediate to 3-hydroxybutyrolactone.

(S)-3-Hydroxybutyrolactone is a key 4-carbon intermediate for the preparation of various drug intermediates including cholesterol lowering drugs. (S)-carnitine, and HIV protease inhibitor drugs, broad spectrum antibiotics.

(R)-3-Hydroxybutyrolactone or (R)-3,4-dihydroxybutyric acid gamma lactose is a key 4-carbon intermediate for the preparation of various drug intermediates. It can also be converted to 1-carnitine, a naturally occurring vitamin and ingredient used in several applications including treatment of various nervous system and metabolic disorders, as an additive in health foods and as a supplement in tonics. The world wide market for carnitine is estimated to be in the hundreds of metric tons. It is currently made by fermentation and by resolution of the d and 1 forms. There is no direct chemical route of any commercial value.

(S)-3-hydroxybutyrolactone can be prepared by the process of Hollingsworth (U.S. Pat. No. 5,374,773). (R)-3-Hydroxybutyrolactone cannot be prepared by the process since this would require the use of a starting material with a 4-linked L-hexane. No such material is known.

1-Malic acid (1-hydroxybutanedioic acid) is a 4-carbon dicarboxylic acid that la obtained in quantity, from apple juice and wine among other fruit juices. R can also be obtained by the hydraulics of fumaric acid and by the fermentation of sugars by some yeasts either as the free acid or as the polyester (polymalic acid). It is relatively inexpensive in isomeric forms.

There are rationally two major commercial routes to (S)-3-hydroxybutyrolactone involving enzymatic resolution. (1) One route to (S)-3-hydroxybutyrolactone involves the reduction of the dimethyl ester of malic acid to (S)-1, 2,4-butanetriol, the preparation of a dioxolane intermediate to protect the 1 and 2 hydroxyl groups followed by oxidation of the 4-hydroxyl group to an aldehyde and then to an acid.

The acid is then deprotected and the dihydroxy compound cyclized to (S)-3-hydroxybutyrolactone. This is shown by the following reaction (Scheme (I)).

Scheme I

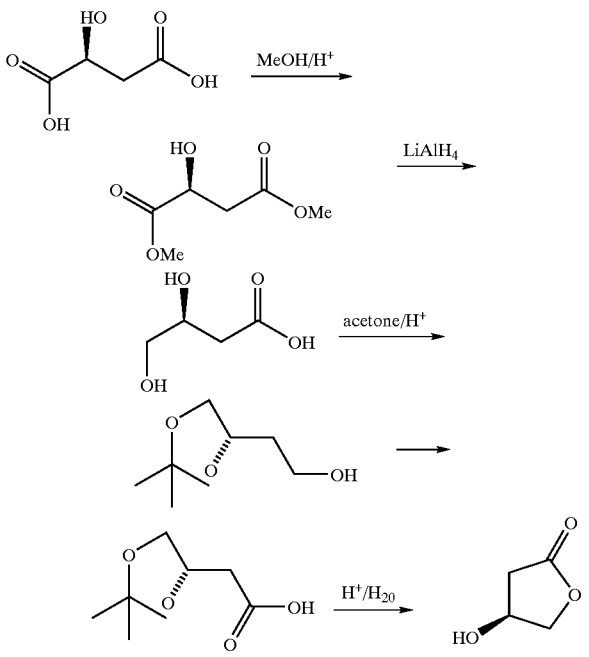

This is a very involved process and has no commercial value. It is complicated by the fan that the dioxolane is contaminated with about 10% of the dioxane. This is difficult to remove and results in the formation of contaminating 2-hydroxybutyrolactone. The process is described in Corey, et al., (E. J. Corey, H. Niwa and I. Knolle. "Total Synthesis of (S)-12-Hydroxy-5,8,14-cis-10-transeicosatetraenoic Acid". J. Amer. Chem Soc. 100 1942–1943(1978)).

(2) Another route involves a process for the direct reduction of malic acid to (S)-3-hydroxybutyric acid and the transformation to (S)-3-hydroxybutyrolactone. This reaction employs the dimethyl sulfide complex of borane and a catalytic amount of sodium borohydride as the reducing system Borane dimethyl sulfide requires specialized equipment to handle and an oxygen free and moisture free environment. It is very toxic and dimethyl sulfide is a very noxious gas. The reducing system is very expensive. The process is described in Saito et al., (S. Saito, T. Hasegawa, M. Inaba, R. Nishida, T. Fujii, S. Nomizu, and T. Moriwaki. "Combination of borane-dimethyl sulfide complex with catalytic sodium tetrahydroborate as a selective reducing agent of a-hydroxy esters, versatile chiral building block from (S)-(−)-malic acid" Chem Letts. 1389–1392 (1984)).

Other references which are pertinent to the present invention are: Arth et al., Liebigs Ann. 2037–2042 (1995) who describe the production of 1,2,4-butanetriol from malic acid using a borane reduction. Tandon, V., et al., J. Org. Chem. 48:767–2769 (1983) who describe the cyclization of 1.2.4-triol to tetrahydrofuran. Boger a al., 46 1208–1210 (1981) who describe a process for producing chiral derivatives from malic acid. Herradon, Asymmetry 2 191–194 (1991) who describes the use of a borane-dimethyl sulfide complex reduction to 1,2,4 butanetriol. This is a difficult process to practice because of problems in handling the butane, Hanessian et al., 199 2146–2147 (1984) describe triol derivatives produced from malic acid using boranes.

The use of alkali metal borohydrides, particularly lithium borohydride, as a reducing and hydrogenerating agent are generally known in the prior art. They are described in U.S. Pat No. 2,683,721 to Schlesinger et al. These are not known for use in preparing hydroxy substituted gamma butyrolactones.

The preparation of la lactones in general is described for instance in Advanced Organic Chemistry 1977, page 363. U.S. Pat. Nos. 3,024,250 to Klein et al., 3,868,370 to Smith, 3,997,569 to Powell, 4,105,674 to De Thomas et al., 4,155,919 to Ratatouille et al., 4,772.729 to Rao, 4,940,805 to Fisher et al., 5,292,939 to Hollingsworth, 5,319,110 to Hollingsworth, 5,374,773 to Hollingsworth, and 5,502,217 to Fuchikami et al. These patents describe diverse processes for the preparation of lactones. They particularly do not describe the use of malic acid as a starting material. The processes described are also relatively complex.

There is a need for an improved process for the preparation of hydroxy butyrolactones and related alcohols and acid derivatives, particularly 4-hydroxy methyl butyrolactone, 3-hydroxybutyrolactone, 1,2,4-butanetriol and 3,4-dihydroxy acid, methyl ester in high yield.

DESCRIPTION OF PREFERRED EMBODIMENTS

The present invention relates to a process for producing a hydroxy substituted compound which comprises: reacting in a reaction mixture a 2-hydroxy substituted alkane diacid lower alkyl diester, wherein the diacid contains 4 to 8 carbon atoms and alkyl contains 1 to 4 carbon atoms, with an alkali metal borohydride in a non-reactive solvent to produce the hydroxy substituted compound.

The present invention relates to a process for the preparation of a hydroxy substituted gamma butyrolactone which comprises: reacting in a reaction mixture a 2-hydroxy substituted alkane diacid lower alkyl diester, wherein the acid contains 4 to 5 carbon atoms and alkyl contains 1 to 4 carbon atoms, with an alkali metal borohydride in a non-reactive solvent at a temperature between about −10° and 60° C. to produce the hydroxy substituted butyrolactone and an alcohol as a by-product.

In the process of the present invention, the preferred lithium borohydride is generated in situ from sodium borohydride and lithium chloride in a solvent, preferably in a mixture of tetrahydrofuran and methanol. This reducing agent is safe to handle without special precaution. It is cheap and readily available. The lithium borohydride is one-tenth the cost of the dimethyl sulfide butane complex of the prior art which is dangerous. The product of the process is isolated by a simple acidification, concentration and extraction. The yields of the process of the present invention are very good. Other alkali metal borohydrides are described in U.S. Pat. No. 2,683,721 to Schlesinger, et al.

The present invention particularly relates to a process for the preparation of a compound selected from the group consisting of 1,2,4-trihydroxybutane and 3,4-dihydroxybutyric acid -1-methyl ester and mixtures thereof which comprises: reacting in a reaction mixture malic acid with a molar excess (preferably more than 100%) of anhydrous methanol in the presence of a catalytic amount of hydrogen ion and at a temperature between about 40° C. and reflux to produce hydroxy butane dioic acid dimethyl ester (2-hydroxy-succinic acid dimethyl ester); and (b) reducing the hydroxy butane dioic acid dimethyl ester with an alkali metal, preferably lithium borohydride in the reaction mixture to produce the compound. The 3-hydroxy gamma butyrolactone can be produced by hydrolyzing the ester.

The ratio of the preferred lithium borohydride to the hydroxy butanedioic acid dimethyl ester determines the predominant product from malic acid which is produced as is shown as follows by Scheme II for the (S) isomer and in Examples 1 to 4:

Scheme II

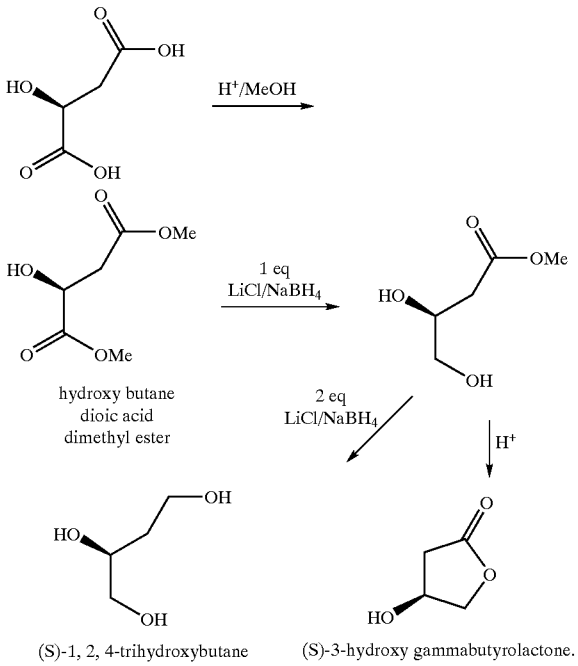

Figure 1:
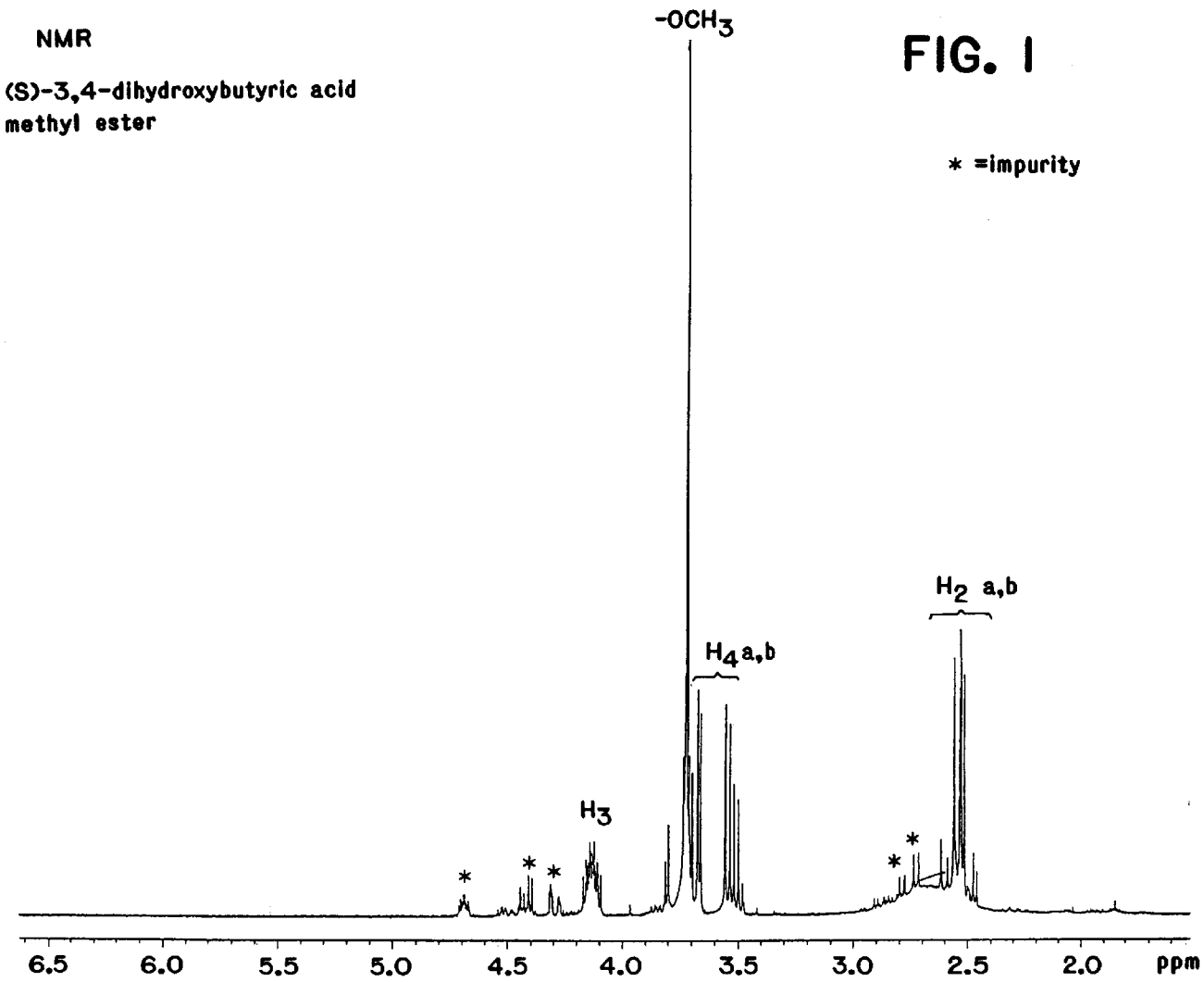
FIGS. 1, 2 and 3 are NMR spectra of (S)-3,4-dihydroxybutyric acid methyl ester (FIG. 1); (S)-1,2,4-butanetriol (FIG. 2) and (S)-3-hydroxy gamma butyric acid lactone (FIG. 3). The asterisk is used to designate impurities. In each instance, the produce are as isolated without further purification. The formulas are shown in FIGS. 1A, 2A and 3A, respectively.
Figure 1A:
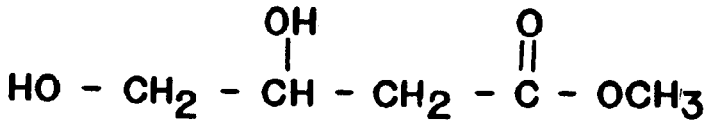
Figure 2A:
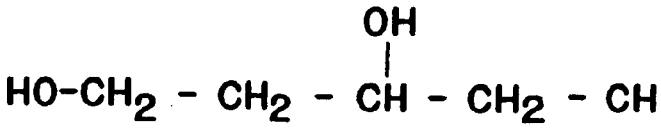
Figure 3A:
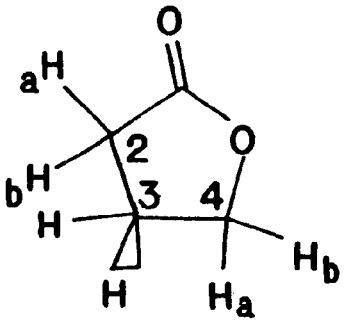
Figure 2:
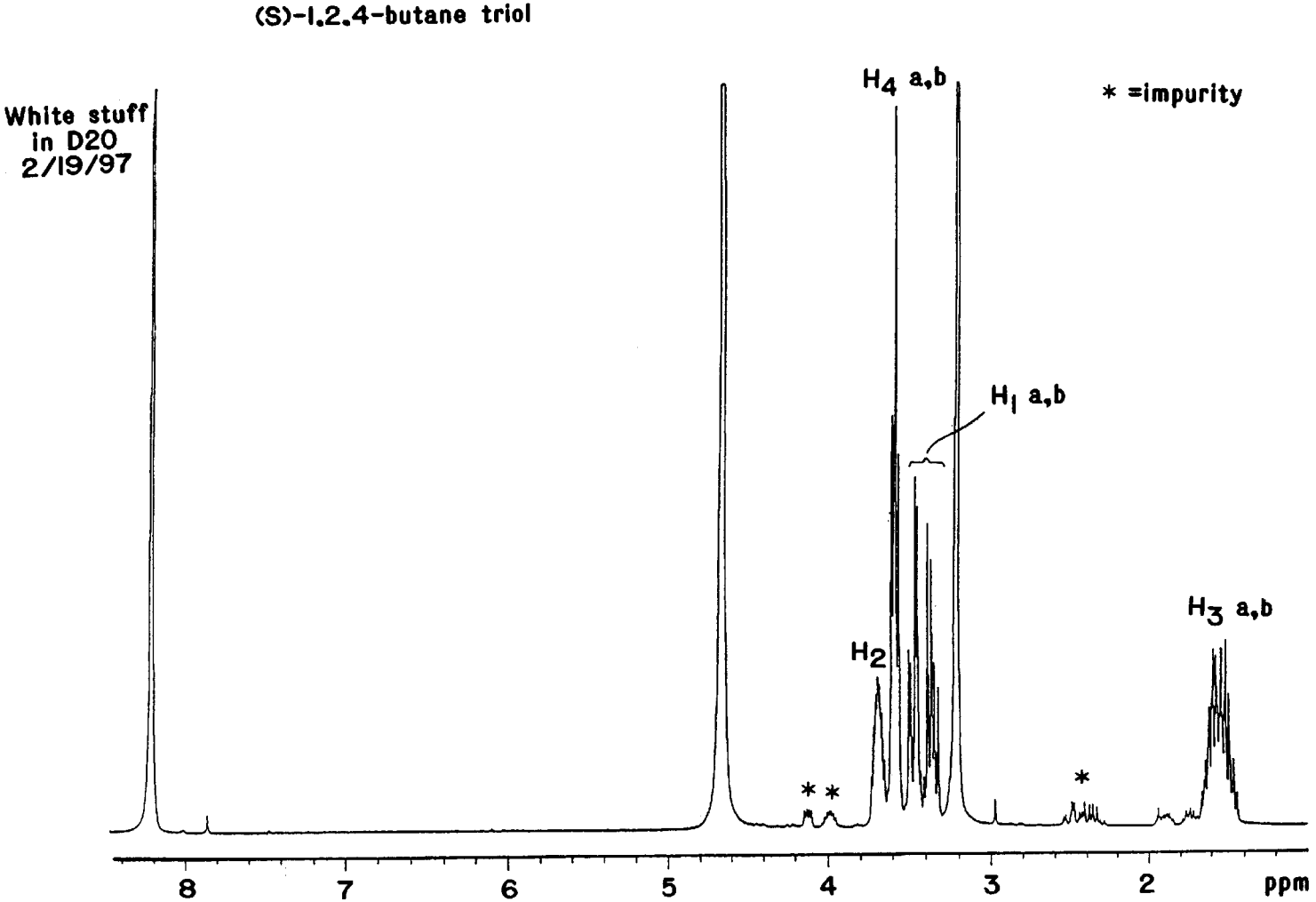
Figure 3:
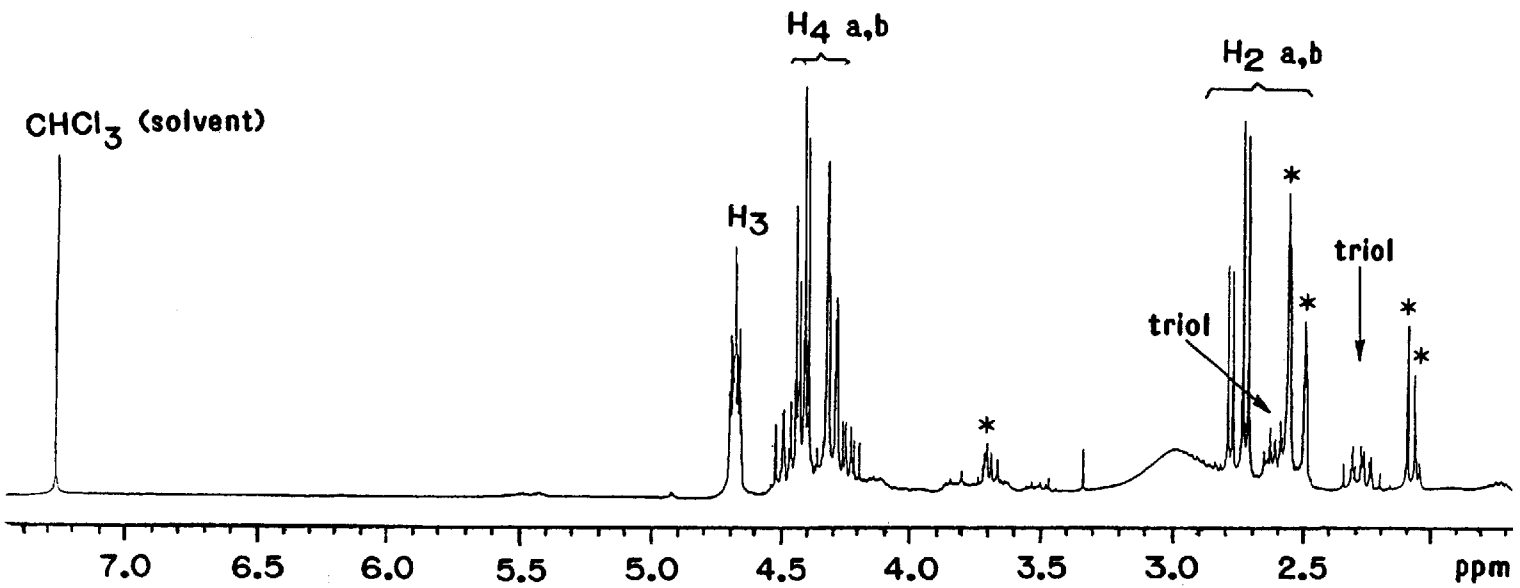

At one equivalent (eq.) the product is essentially the lactone in the presence of added acid. With two (2) equivalents of the lithium borohydride, the product is essentially the (S)1, 2,4-trihydroxybutane. This can be seen from the following examples. The NMR spectra am shown in FIGS. 1 to 3 with the formulas shown in FIGS. 1A, 2A and 3A.

The Process of the present invention has the advantage that the steps are performed in the same reaction vessel. The yields are 88% a better of the 3-hydroxybutyrolactone. The yield of the 1.2,4-trihydroxybutane is generally greater than 96% with a molar excess of the lithium borohydride. The preferred reaction temperature is between −10° and 60° C.

The reaction after the formation of 3.4-dihydroxybutyric acid-1-methyl ester as shown is Scheme II, as a result of the reduction reaction, is heated with acid or methanol to form the 3-hydroxybutyrolactone. Preferably a strong acid is used for the acidification, such as phosphoric acid or hydrochloric acid. After adding water and extracting the 3-hydroxybutyrolactone with a solvent such as ethyl acetate, the 1,2,4-trihydroxybutane is left to the water layer.

It will be appreciated that the 3.4-hydroxybutyric acid methyl ester can be converted to the acid or to a metal salt (preferably alkali metal salt). There is no advantage to this step if the final product is the 3-hydroxybutyrolactone.

Example 5 shows the preparation of (S)-4-hydroxymethyl gamma butyrolactone. The reaction Scheme III is as follows.

Scheme III

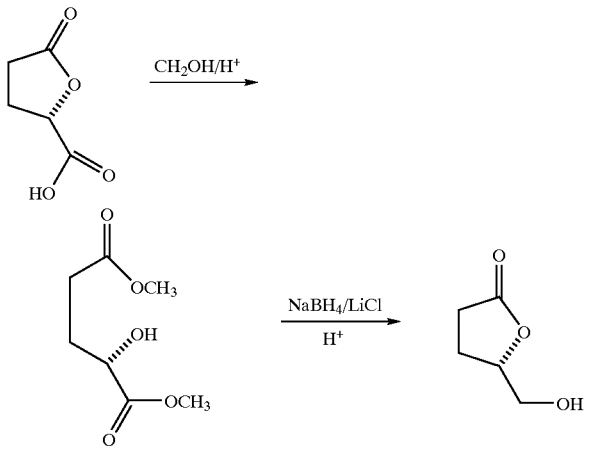

Various solvents can be used to extract the reaction products from the reaction mixture. The 3-hydroxybutane and 4-hydroxy methyl butyrolactone are soluble in ethyl acetate. The 1,2,4-trihydroxybutane is soluble in water. Other isolation techniques can be used. If the product is an intermediate to a further product the reaction mixture may be used without isolating the product.

EXAMPLE 1

Direct Reduction of Malic Acid to Lactone (S)-Isomer

L-Malic acid (50 grams, 0.37 moles) was refluxed for 3 hours with 500 ml of anhydrous methanol containing 1% hydrogen chloride to form the dimethyl ester (Scheme II). The solution was concentrated to a syrup and dissolved in 200 ml of tetrahydrofuran. Anhydrous lithium chloride (32 grams, 0.74 moles) was added followed by sodium borohydride (16 grams, 0.42 moles) and methanol (80 ml) to provide the reducing agent. The mixture was stirred at room temperature (25° C.) for 6 hours, filtered, concentrated to dryness, treated with methanol (500 ml) containing hydrochloric acid (50 ml) and concentrated to dryness on a rotary evaporator at a bath temperature of 35° C. A-further 500 ml of methanol was added and the solution concentrated again. The process was repeated twice again and the final syrup partitioned between ethyl acetate and water 20 ml: 400 ml. The ethyl acetate layer was recovered, dried and concentrated to yield (S)-3-hydroxybutyrolactone (34 grams, 90%).

EXAMPLE 2

Direct Reduction of Malic Acid to Lactone (R)-Isomer

D-Malic acid (1 gram, 0.0075 moles) was refluxed for 3 hours with 10 ml of anhydrous methanol containing 1% hydrogen chloride to form the dimethyl ester (Scheme II). The solution was concentrated to a syrup and dissolved in 4 ml of tetrahydrofuran. Anhydrous lithium chloride (0.6 grams. 0.014 moles) was added followed by sodium borohydride (0.32 grams, 0.0084 moles) and methanol (2 ml) to provide the reducing agent. The mixture was stirred at room temperature(25° C.) for 6 hours, filtered, concentrated to dryness, treated with methanol (10 ml) containing hydrochloric acid (1 ml) and concentrated b dryness on a rotary evaporator at a bath temperature of 35° C. A further 10 ml of methanol was added and the solution concentrated again. The process was repeated twice again and the final syrup partitioned between ethyl acetate and water, 0.4 of: 8 ml. The ethyl acetate layer was recovered, dried and concentrated to yield (R)-3-hydroxybutyrolactone (0.6 grams, 88%).

EXAMPLE 3

Direct Reduction of L-Malic Acid to (S)1,2,4-Trihydroxybutane

L-Malic acid (134 grams. 1 mole) was dissolved in methanol (1,200 ml) and concentrate hydrochloric acid (12 ml) was added The solution was heated under reflux in a 3 liter flask equipped with a calcium chloride drying tube for 4 hours to provide the dimethyl ester (Scheme II) and then concentrated to a syrup under vacuum (water aspirator). More methanol (200 ml) was added and the solution concentrated again to remove tracts of acid. The syrup was then dissolved in tetrahydrofuran (800 ml) and sodium borohydride (80 grams, 2.1 moles) and lithium chloride (126 grams. 3 moles) added. The sodium borohydride was added first carefully over a period of 10 minutes. There should be very little effervescence if all of the acid was removed earlier. The deals was cooled to 30° C. and the mixture was stirred for 15 minutes and then methanol (600 ml) was added over a period such that the temperature does not exceed 30° C. Concentrated (88%) phosphoric acid (1 mole) was carefully added to destroy excess reagent (cooling if necessary). The mixture was then filtered through Whatman #1 paper and concentrated to a syrup to yield 130 grams of crude 1.2.4-trihydroxybutane.

EXAMPLE 4

Direct Reduction of L-Malic Acid to (S)-1,2.4-Trihydroxybutane

L-Malic acid (134 grams, 1 mole) was dissolved in methanol (1,200 ml) and concentrate hydrochloric acid (12 ml) was added The solution was heated under reflux in a 3 liter flask equipped with a calcium chloride drying tube for 4 hours and then concentrated to a syrup under vacuum (water aspirator) to provide the dimethyl ester (Scheme II). More methanol (200 ml) was added and the solution concentrated again to remove trams of acid. The syrup was then dissolved in tetrahydrofuran (800 ml) and lithium chloride (126 grams, 3 moles) and sodium borohydride (80 grams. 2.1 moles) added. The sodium borohydride was added carefully. There should be very little effervescence if all of the acid was removed earlier. The flask was fitted with a condenser and drying robe and the mixture was stirred for 15 minutes and then methanol (600 ml) was added over a 5 minute period. The first 400 ml was added at once and the remaining 200 ml was then added There is an increase in temperature of the mixture to 52°–54° C. resulting in a gentle reflux with a steady release of hydrogen especially as the last 200 ml of methanol was added. The reaction mixture was tut cooled ova this period. The temperature drops back to room temperature after 1 hour and the reaction mixture wan then refluxed for 4 hours and cooled. It was diluted with 400 ml of methanol and concentrated HCl (200 ml) was carefully added to destroy excess reagent (cooling if necessary). The mixture was then filtered through Whatman #1 paper, concentrated to a syrup and desalted through A cation exchange (DOWEX 50WX4-50, Made by Dow Chemical Midland Mich.) and concentrated to a syrup which was concentrated 4 times from methanol (500 ml) an equal vol of water added and extracted twice with 500 ml of ethyl acetate (to remove lactone if there is under-reduction) and the water fraction concentrated. Yields of crude product at end of ethyl acetate extract: 3-hydroxybutyrolactone, 37 grams; 1,2,4-trihydroxybutane 126 grams.

EXAMPLE 5

Selective Reduction of (S)-4-Carboxy-γ-Butyrolactone to (S)4-Hydroxymethyl-γ-Butyrolactone. (Scheme III)

(S)-4-carboxy-γ-butyrolactone (130 grams, 1 mole) was dissolved in methanol (1,200 ml) and concentrated hydrochloric acid (12-ml) was added. The solution was heated under reflux in a 3 liter flask equipped with a calcium chloride drying tube for 4 hours to form the dimethyl ester (Scheme III). The mixture was then treated with calcium carbonate (20 grams) to remove acid and then concentrated to ~300 ml under vacuum (water aspirator). The syrup was then dissolved in tetrahydrofuran (800 ml) and sodium borohydride (20 grams, 1.05 moles) and lithium chloride (63 grams, 1.5 moles) added as the reducing agent. The sodium borohydride was added first carefully over a period of 10 minutes. Very little effervescence was observed if all of the acid was removed earlier. The flask was cooled to 30° C. and the mixture stirred for 15 minutes and then methanol (300 ml) was added over a period such that the temperature does not exceed 30° C. Concentrated (88%) phosphoric acid (½ mole) was carefully added to destroy excess reagent cooling if necessary). The mixture was then filtered through Whatman #1 paper and concentrated to a syrup. The syrup was taken up in ethyl acetate and filtered the filtrate concentrated and redissolved in water (400 ml). The solution was passed over a mixed bed ion exchange resin to remove salts. On concentration it yielded 100 grams (87%) of the desired product In a similar manner, other hydroxy alkyl substituted butyrolactones can be prepared with 6 to 8 carbon atoms.

It is intended that the foregoing description be only illustrative of the present invention and that the present invention be limited only by the hereinafter appended claims.

I claim:

[1. A process for producing a hydroxy substituted compound which comprises: reacting in a reaction mixture a 2-hydroxy substituted alkane diacid lower alkyl diester wherein the diacid contains 4 to 8 carbon atoms and alkyl contains 1 to 4 carbon atoms, with an alkali metal borohydride in a non-reactive solvent to produce the hydroxy substituted compound.]

2. A process for the preparation of a hydroxy substituted gamma butyrolactone which comprises:

reading in a reaction mixture a 2-hydroxy substituted alkane diacid lower alkyl diester, wherein the diacid contains 4 in 5 carbon atoms and alkyl contains 1 to 4 carbon atoms, with an alkali metal borohydride in a non-reactive solvent at a temperature between about −10° and 60° C. to produce the hydroxy substituted gamma butyrolactone and an alcohol as a by-product.

3. The process of claim 2 wherein the diester is 4-carboxymethyl-4-hydroxybutyric acid-1-methyl ester and wherein the hydroxy substituted gamma butyrolactone is 4-hydroxymethyl butyrolactone.

4. The process of any one of claims 2 or 3 wherein the ester and the hydroxy substituted gamma butyrolactone are isomers.

5. The process of any me of claims 2 or 3 wherein one ester and the hydroxy substituted gamma butyrolactone are isomers, and wherein the isomers are (S) isomers.

6. The process is any one of claims 2 or 3 wherein the ester and the hydroxy substituted gamma butyrolactone are isomers and wherein the isomer are (R) isomers.

7. The process of any one of claims 2 or 3 wherein as an additional step the reaction mixture is acidified and heated to volatilize the alcohol from the vendors mixture and the hydroxy substituted gamma, butyrolactone.

8. The process of claim 2 wherein the hydroxy substituted gamma butyrolactone is extracted from the reaction mixture with ethyl acetate.

9. The process of claim 2 wherein in the ester the lower alkyl is methyl, wherein the alkylene contains five carbon atoms and wherein the butyrolactone is 4-hydroxymethyl gamma butyrolactone.

[10. A process for the preparation of a compound selected from the group consisting of 1,2,4-trihydroxybutane and 3,4-dihydroxybutyric acid -1-methyl ester and mixtures thereof which comprises:

(a) reacting in a reaction mixture malic acid with a molar excess of anhydrous methanol in the presence of a catalytic mount of hydrogen ion end at a temperature between about 40° and reflux to produce hydroxybutane dioic acid di methyl ester; and (b) reducing the hydroxybutane dioic acid dimethyl ester with an alkali metal borohydride to produce the compound.]

11. The process of claim [10] *27* wherein about one equivalent of the alkali metal borohydride is reacted with the hydroxybutane dioic acid dimethyl ester [and] *to produce* [wherein the compound is substantially] the 3.4-hydroxybutyric acid methyl ester.

[12. The process of claim 10 wherein about three equivalents of the alkali metal borohydride is reacted with the hydroxy butane dioic acid dimethyl ester and the compound is substantially the 1,2,4-trihydroxybutane.]

[13. The process of any one of claims 10, 11 or 12 wherein the malic acid is an isomer.]

[14. The process of any one of claims 11 or 12 wherein the malic acid is an isomer and the humid is the (S) isomer.]

[15. The process of any one of claim 11 or 12 wherein the malic acid is an isomer and the isomer is the (R) isomer.]

[16. The process of claim 10 wherein the 3.4-dihydroxybutyric acid methyl ester is extracted from the reaction mixture with ethylacetate.]

[17. The process of claim 10 wherein the reaction mixture in step (a) is refluxed.]

18. The process of claim 11 wherein as an additional step the 3,4-dihydroxy butyric acid -1-methyl ester is acidified and heated to volatilize the methanol from the reaction mixture from step (a) [and] to produce [the hydroxylactone] *4-hydroxymethyl butyrolactone.*

19. The process of claim 18 wherein about one equivalent of the *alkali metal borohydride which is* lithium borohydride is reacted with the hydroxy butane dioic acid dimethyl ester to produce the 3,4-dihydroxybutyric acid -1-methyl ester.

[20. The process of claim 10 wherein the 1,2,4-trihydroxybutane is extracted from the reaction mixture using water.]

21. The process of claim 19 wherein the malic acid is as the (R) isomer and the [compound] *3,4 dihydroxybutyric acid-1-methyl ester* produced is the (R) isomer.

22. The process of claim 19 wherein the malic acid is as the (S) isomer and the [compound] *3,4-dihydroxy butyric acid-1-methyl ester* produced is the (S) isomer.

[23. The process of claim 10 wherein in addition the 3,4-hydroxy butyric acid -1-methyl ester is separated and reacted with an acid to form 3-hydroxy gamma butyrolactone.]

[24. The process of claim 1 wherein the alkali metal borohydride is lithium borohydride.]

25. The process of claim 2 wherein the alkali metal borohydride is lithium borohydride.

[26. The process of claim 10 wherein the alkali metal borohydride is lithium borohydride.]

*27. A process for the preparation of 3,4-dihydroxybutyric acid-1-methyl ester which comprises:*

(*a*) *reacting in a reaction mixture malic acid with a molar excess of anhydrous methanol in the presence of a catalytic amount of hydrogen ion and at a temperature between about 40° and reflux to produce hydroxybutane dioic acid dimethyl ester; and*

(*b*) *reducing the hydroxybutane dioic acid dimethyl ester with an alkali metal borohydride to produce the 3,4-dihydroxybutyric acid-1-methyl ester.*

*28. The process of any one of claims 11 or 27 wherein the malic acid is an isomer.*

*29. The process of claim 11 wherein the malic acid is an isomer and the isomer is the* (*S*) *isomer.*

*30. The process of claim 11 wherein the malic acid is an isomer and the isomer is the* (*R*) *isomer.*

*31. The process of claim 27 wherein the 3,4-dihydroxybutyric acid methyl ester is extracted from the reaction mixture with ethylacetate.*

*32. The process of claim 27 wherein the reaction mixture in step* (*a*) *is refluxed.*

*33. The process of claim 27 wherein in addition the 3,4-hydroxy butyric acid-1-methyl ester is separated and reacted with an acid to form 3-hydioxy gamma butyrolactone.*

*34. The process of claim 27 wherein the alkali metal borohydride is lithium borohydride.*

* * * * *

UNITED STATES PATENT AND TRADEMARK OFFICE

CERTIFICATE OF CORRECTION

PATENT NO. : RE 38,324 E
DATED : November 18, 2003
INVENTOR(S) : Rawle I. Hollingsworth It is certified that error appears in the above-identified patent and that said Letters Patent is hereby corrected as shown below:

Column 1,
Line 24, “favors” should be -- flavors --.
Line 27, “to Inone” should be -- to Inoue --.
Lines 28 and 29, “pro ass” should be -- process --.
Line 35, “and HIV” should be -- anti HIV --.
Line 39, “gamma lactose” should be -- gamma lactone --.
Line 53, “L-hexane” should be -- L-hexose --.
Line 55, “that la” should be -- that is --.
Line 56, “R can” should be -- It can --.
Line 57, “the hydraulics” should be -- the hydration --.
Line 61, “are rationally” should be -- are currently --.

Column 2,
Scheme I, line 17, “ 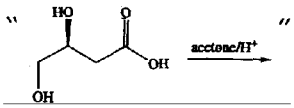 ” should be -- 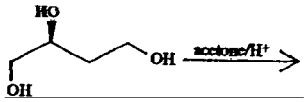 --

Line 33, “the fan” should be -- the fact --.
Line 45, “system Borane” should be -- system. Borane --.
Line 59, “48:767-2769 (1983)” should be -- 48:2767-2769 (1983) --.
Line 60, “Boger a al.,” should be -- Boger et al., --.
Line 65, “butane, Han-” should be -- borane. Han --.

Column 3,
Line 7, “la lactones” should be -- of lactones --.
Line 11, “Ratatouille et al.,” should be -- Ramiouille et al., --.
Line 30, “the produce” should be -- the products --.
Line 59, “butane” should be -- borane --.

Column 4,
Line 50, “am shown” should be -- are shown --.
Line 54, “88% a better” should be -- 88% or better --.
Line 65, “left to the water” should be -- left in the water --.

Column 5,
Line 65, “concentrated b dryness” should be -- concentrated to dryness --.

UNITED STATES PATENT AND TRADEMARK OFFICE

CERTIFICATE OF CORRECTION

PATENT NO. : RE 38,324 E
DATED : November 18, 2003
INVENTOR(S) : Rawle I. Hollingsworth It is certified that error appears in the above-identified patent and that said Letters Patent is hereby corrected as shown below:

Column 6,
Line 2, "0.4 of: 8 ml." should be -- 0.4 ml : 8 ml. --.
Line 16, "remove tracts of" should be -- remove traces of --.
Line 22, "deals was" should be -- flask was --.
Line 35, "added The" should be -- added. The --.
Line 40, "remove trams" should be -- remove traces --.
Line 46, "drying robe" should be -- drying tube --.
Line 49, "added There" should be -- added. There --.
Line 53, "was tut cooled ova" should be -- was not cooled over --.
Line 55, "wan then" should be -- was then --.
Line 59, "through A" should be -- through a --.

Column 7,
Lines 19 and 20, "($^1/_2$ mole)" should be -- (1/3 mole) --.
Line 20, "cooling" should be -- (cooling --.
Line 23, "filtered the filtrate" should be -- filtered, the filtrate --.
Line 44, "reaction" should be -- reacting --.
Line 46, "contains 1 to 4" should be -- contains 4 to 5 --.
Line 58, "any me" should be -- any one --.
Line 58, "wherein one" should be -- wherein the --.
Line 66, "vendors" should be -- reaction --.

Column 8,
Line 14, "mount" should be -- amount --.
Line 32, "the humid" should be -- the isomer --.

UNITED STATES PATENT AND TRADEMARK OFFICE

CERTIFICATE OF CORRECTION

PATENT NO. : RE 38,324 E
DATED : November 18, 2003
INVENTOR(S) : Rawle I. Hollingsworth It is certified that error appears in the above-identified patent and that said Letters Patent is hereby corrected as shown below:

Column 10,
Line 9, "3-hydioxy" should be -- 3-hydroxy --.

Signed and Sealed this

Twentieth Day of April, 2004

JON W. DUDAS
*Acting Director of the United States Patent and Trademark Office*